United States Patent [19]
Weaver

[11] Patent Number: 5,389,069
[45] Date of Patent: Feb. 14, 1995

[54] METHOD AND APPARATUS FOR IN VIVO ELECTROPORATION OF REMOTE CELLS AND TISSUE

[75] Inventor: James C. Weaver, Sudbury, Mass.

[73] Assignee: Massachusetts Institute of Technology, Cambridge, Mass.

[21] Appl. No.: 122,809

[22] Filed: Sep. 17, 1993

Related U.S. Application Data

[63] Continuation of Ser. No. 705,778, May 28, 1991, abandoned, which is a continuation-in-part of Ser. No. 331,263, Mar. 30, 1989, Pat. No. 5,019,034, which is a continuation-in-part of Ser. No. 146,343, Jan. 21, 1988, abandoned.

[51] Int. Cl.$^6$ ............................................. A61N 1/30
[52] U.S. Cl. ..................................... 604/21; 435/173.6; 604/51
[58] Field of Search .................. 604/20, 21, 49, 51, 604/52; 128/784, 786; 435/173.6

[56] References Cited

U.S. PATENT DOCUMENTS

| | | | |
|---|---|---|---|
| 578,611 | 3/1897 | Rively | 604/21 |
| 3,078,850 | 2/1963 | Schein et al. | 128/419 D |
| 3,614,955 | 10/1971 | Mirowski | 128/419 D |
| 3,680,544 | 8/1972 | Shinnick et al. | 604/21 |
| 4,055,799 | 10/1977 | Coster et al. | |
| 4,081,340 | 3/1978 | Zimmerman et al. | |
| 4,154,668 | 5/1979 | Zimmerman et al. | |
| 4,220,916 | 9/1980 | Zimmerman et al. | |
| 4,411,648 | 10/1983 | Davis et al. | 604/21 |
| 4,578,168 | 3/1986 | Hofmann | |
| 4,663,292 | 5/1987 | Wong et al. | |
| 4,695,547 | 9/1987 | Hilliard et al. | |
| 4,764,473 | 8/1988 | Matschke et al. | |
| 4,784,737 | 11/1988 | Ray et al. | 204/180.1 |
| 4,822,470 | 4/1989 | Chang | |
| 4,955,378 | 9/1990 | Grasso | 128/788 |
| 4,979,948 | 12/1990 | Geddes et al. | 128/786 |
| 5,007,995 | 4/1991 | Takahashi et al. | 204/299 R |
| 5,019,034 | 5/1991 | Weaver et al. | 604/20 |
| 5,047,007 | 9/1991 | McNicols et al. | 604/20 |
| 5,098,843 | 3/1992 | Calvin | 435/287 |

OTHER PUBLICATIONS

Okino, et al., *Journal of Japan Soc. for Cancer Therapy*, 22(8):337 (1987).
Kanesada, et al., *Journal of Japan Soc. for Cancer Therapy*, 22(8):338 (1987).
Okino, et al., *Japan Journal of Cancer Research*, 46:420 (1987).
Mir et al., "Improvement of Anticancer Electrochemotherapy", *Proceedings of the American Associate for Cancer Research*, 30, p. 571 (1989).
Mir et al., "Pharmacological Applications of Electropermeabilization of Living Cells", *Lab. de Biochimie–Enzymologie*, Institute Gustave–Roussy 94805 Villejuif Cadex–France.
Mir et al., "Potentiation of Bleomycin by Local Electric Pulses: Experimental Anticancer Electrochemotherapy", *Proceedings of the American Association for Cancer Research*, 30, p. 440 (1990).

(List continued on next page.)

*Primary Examiner*—Ralph A. Lewis
*Attorney, Agent, or Firm*—Hamilton, Brook, Smith & Reynolds

[57] ABSTRACT

A method and apparatus is disclosed for causing electroporation of remote cells and tissue, in vivo. The method includes directing an electrically conductive penetrator into an organism to a point which is approximate to the cells and/or tissue. An electrode is disposed at a surface of the organism, whereby a voltage applied between the electrically conductive penetrator and the electrode will cause electroporation of the cells and/or tissue. A voltage is applied between the electrically conductive penetrator and the electrode in an amount sufficient to cause electroporation of the cell or tissue. The method can also include treating remote tissue, in vivo, with a chemical agent, wherein the chemical agent is disposed in the organism in an amount sufficient to treat the cell or tissue during electroporation.

23 Claims, 3 Drawing Sheets

OTHER PUBLICATIONS

Mir et al., 'Electrochemotherapy Potentiation of Antitumour Effect of Bleomycin by Local Electric Pulses38 , *Eur. F Cancer*, 27(1):68–72 (1991).

Okino et al., "Effects of a High-Voltage Electrical Impulse and an Anticancer Drug on In Vivo Growing Tumors", *Jpn. J. Cancer Res.*, 78(12):1319–1321 (1987).

Heroux et al., "Assessment of Trauma in Tissues By Electrical Impedance Measurements", *Electromagnetics in Biology and Medicine*, pp. 215–221 (1991).

Bhatt et al., "Rhabdomyolysis Due to Pulsed Electric Fields", *Plastic and Reconstructive Surgery*, 86(1):1–11 (1990).

Heller et al., "Transfer of Human Membrane Surface Components by Incorporating Human Cells into Intact Animal Tissue by Cell–Tissue Electrofusion In Vivo", *Biochimica et Biophysica Acta.*, vol. 1024, pp. 185–188 (1990).

Titomirov et al., "In Vivo Electroporation and Stable Transformation of Skin Cells of Newborn Mice by Plasmid DNA", *Biochimica et Biophysica Acta.*, vol. 1088, pp. 131–134 (1991).

Zimmerman et al, "Effects of External Electrical Fields on Cell Membranes", *Bioelectrochemistry and Bioenergetics* 3, 58–83 (1976).

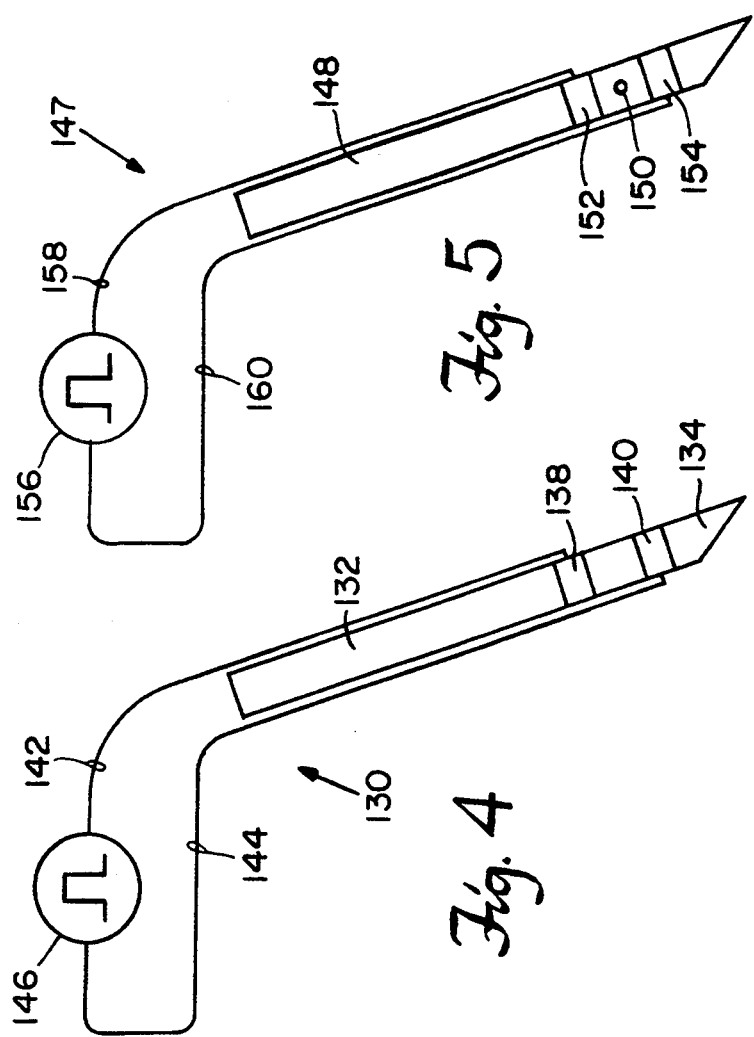
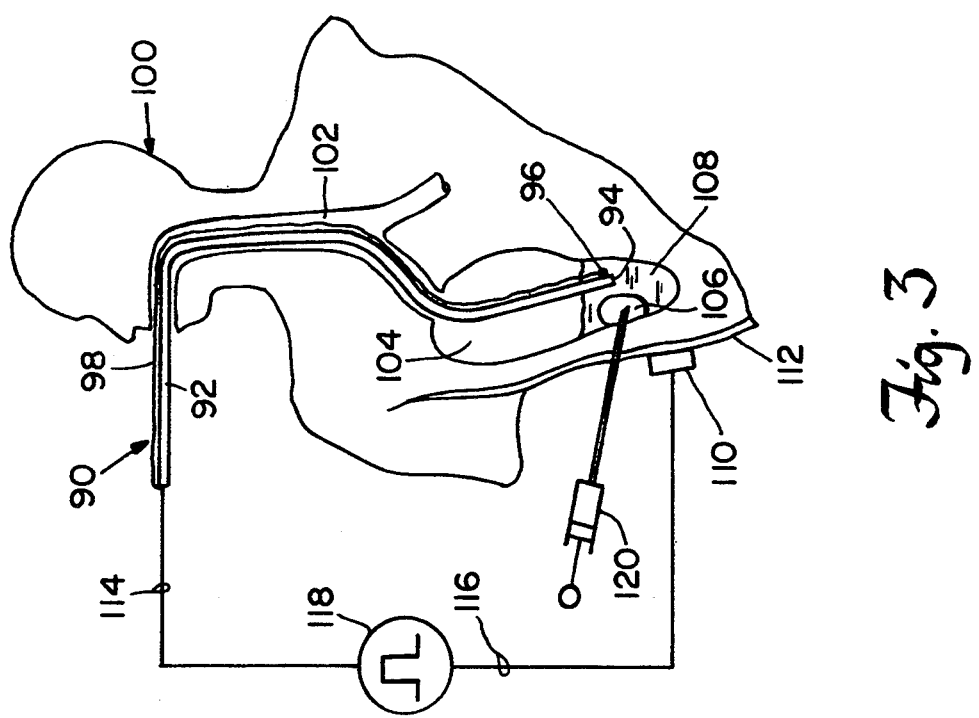

METHOD AND APPARATUS FOR IN VIVO ELECTROPORATION OF REMOTE CELLS AND TISSUE

RELATED APPLICATIONS

This application is a continuation of application Ser. No. 07/705,778, filed on May 28, 1991, now abandoned which is a continuation-in-part of prior Ser. No. 07/331,263, filed Mar. 30, 1989, now U.S. Pat. No. 5,019,034, which is a continuation-in-part of Ser. No. 07/146,343, filed Jan. 21, 1988, now abandoned.

BACKGROUND OF THE INVENTION

Many drugs and chemical agents are known to be effective in treatment of diseased tissue, such as tumors. However, such agents also often have deleterious side effects when introduced into the organism in sufficient dosage to treat the targeted tissue.

One attempt to selectively treat diseased tissue, such as tumors, is development of chemical agents which selectively affect only tumor cells. However, such chemical agents typically are only partially selective for the diseased tissue and often have a deleterious effect on healthy cells. Another attempt to selectively treat diseased tissue is to inject the chemical agent directly into the diseased tissue mass. However, the effect of chemical agents on diseased tissue is often dependent upon delivery of the chemical agent across cell membranes of the cells in the tissue mass as opposed to simply injecting the chemical agent into the tissue. Further, chemical agents which are injected into diseased tissue typically enter the bloodstream and are transported away from the targeted tissue mass before they have a significant therapeutic affect on the tissue mass into which they were injected.

Another attempt to selectively treat diseased tissue is by electroporation. Generally, electroporation is a method of increasing the permeability of tissue and cell membranes. The increased permeability allows transport, or migration, of chemical agents through the tissue or across cell membranes into cells. For example, electroporation can include applying a voltage across tissue in vitro to cause the permeability of the tissue and cell membranes of cells in the tissue to increase. If the tissue is in the presence of a suitable chemical agent, the chemical agent can then migrate across the tissue or into cells of the tissue. Electroporation has also been used to deliver drugs to tissue, in vivo, by applying electrodes to the surface of an organism and applying a voltage between the electrodes which exposes the tissue to an electric field. The tissue thereby becomes electroporated and allows delivery of a chemical agent, such as a drug, which has been applied either topically to the organism or injected into the blood stream of the organism, across the electroporated tissue and into cells of the electroporated tissue.

However, in vivo electroporation is generally limited to tissue which is proximate to the surface of the organism. For example, tissue requiring delivery of a drug or other chemical agent in vivo is limited to tissue which is close to the skin of the organism where the electrodes are disposed. Therefore, tissue which would otherwise be treatable by drug delivery or chemotherapy, such as tumors, are relatively unaffected by known methods of electroporation.

Therefore, a need exists for a new method and apparatus for treating remote tissue, in vivo, which overcomes or minimizes the above-listed problems.

SUMMARY OF THE INVENTION

The present invention relates to a new method and apparatus for treating at least one cell, in vivo.

The method includes directing an electrically conductive penetrator into an organism to a point which is proximate to the cell. An electrode is disposed at the organism, whereby a voltage is applied between the electrically conductive penetrator and the electrode. A voltage is then applied between the electrically conductive penetrator and the electrode in an amount sufficient to cause electroporation of the cell, whereby a chemical agent in the organism passes across the cell membrane into the electroporated cells, thereby treating the cell.

The apparatus includes a penetrator, having a penetrating end, for penetration of an organism. A first electrode is disposed at the penetrating end of the penetrator, whereby the first electrode is disposed adjacent to cell when the penetrator has penetrated the organism. The apparatus also includes a second electrode for placement at the organism, whereby a voltage applied between the first electrode and the second electrode will cause electroporation of the cell. Suitable means are connected to the first electrode and the second electrode for applying a voltage between the first and second electrodes in an amount sufficient to electroporate the cell, whereby a chemical agent in the organism migrates across cell membrane and into the electroporated cell, thereby treating said cell.

This invention has many advantages. Tissue which is remote from the surface of the organism can be electroporated by penetrating the organism with an electrically conductive penetrator which disposes an electrode in close proximity to the tissue to be treated. Further, drugs or other chemical agents, such as DNA and other agents for gene therapy, can be introduced to the tissue through the electrically conductive penetrator for delivery of the chemical agent into the tissue at a point close to the electrode, where electroporation of the tissue is greatest. In addition, drugs which have strong side effects when employed in the absence of electroporation, can be employed to effect such tissue in significantly lower dosages, thereby significantly diminishing such side effects. Similarly, cytotoxic chemicals which are not selective for diseased tissue can be employed to treat remote tissue without significantly damaging surrounding healthy tissue. Also, diseased tissue, such as tumors which are not otherwise operable and are relatively resistant to drugs and other chemical agents at safe dosage levels, can be treated by the method and apparatus of the present invention. Treatment of tissue, by genetically altering at least a portion of the cells of the tissue, can be localized by introducing a suitable chemical agent, such as DNA, to a desired site, such as a blood vessel wall or a targeted organ.

BRIEF DESCRIPTION OF THE DRAWINGS

FIG. 3 is a section view of a third embodiment of the invention which includes an endoscope having an electrode disposed therein.

FIG. 4 is a side view of a fourth embodiment of the invention which includes two electrodes on a catheter.

FIG. 5 is a side view of a fifth embodiment of the invention wherein a catheter defines an orifice disposed between two electrodes on the catheter.

DETAILED DESCRIPTION OF THE INVENTION

The features and other details of the method and apparatus of the invention will now be more particularly described with reference to the accompanying drawings and pointed out in the claims. It will understood that the particular embodiments of the invention are shown by way of illustration and not as limitations of the invention. The principle features of this invention can be employed in various embodiments without departing from the scope of the invention.

Figure 1:
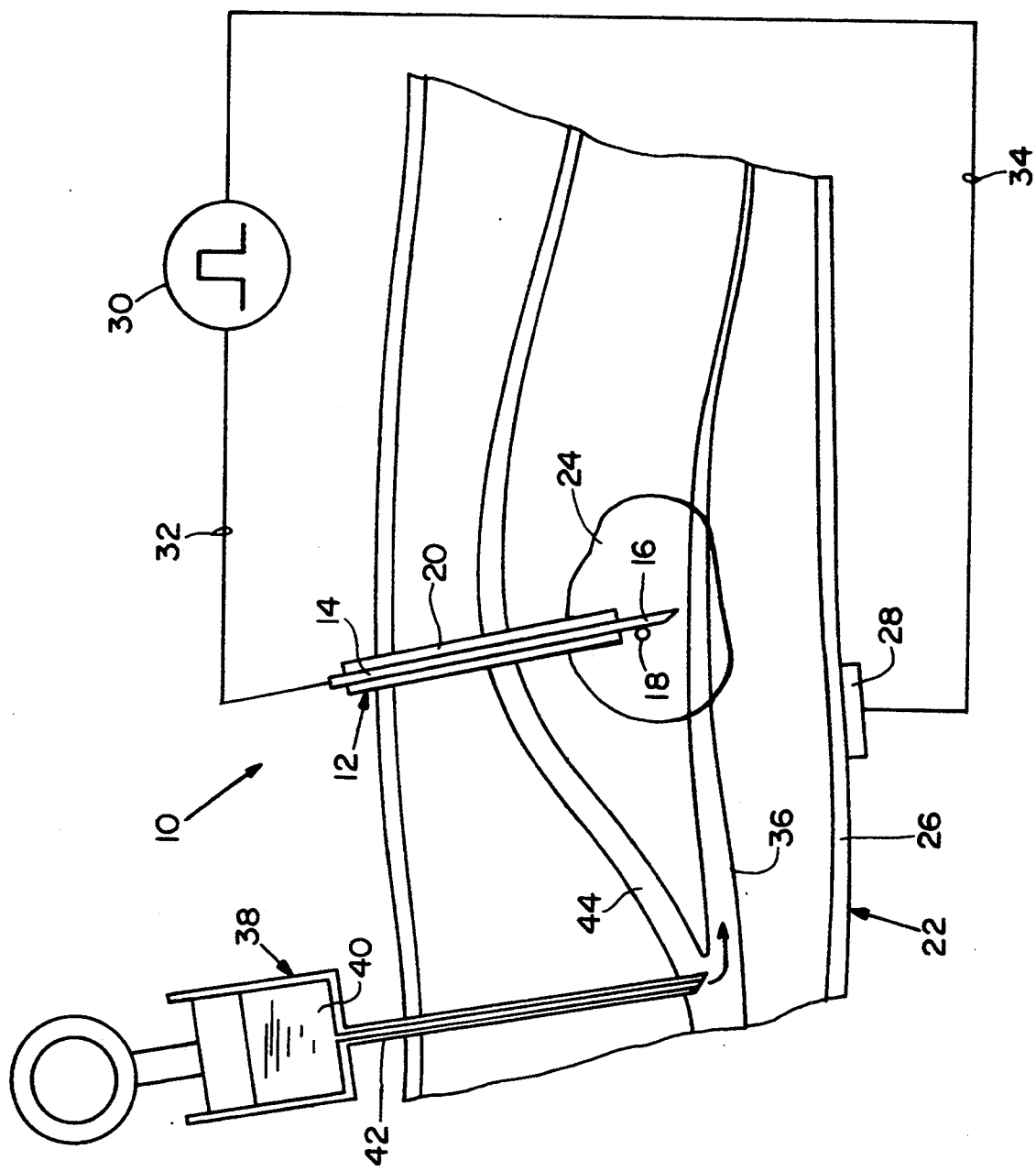
FIG. 1 is a section view of one embodiment of the invention during treatment of a tumor which is remotely disposed within an organism.

In one illustration of the invention, shown in FIG. 1, apparatus 10 includes penetrator 12. Penetrator 12 includes electrically conductive rod 14 having a penetrating end 16. Electrically conductive rod 14 can be rigid or flexible. First electrode 18 is disposed at penetrating end 16. Penetrating end 16 is suitably sharp for delivery into organism 22. Sheath 20 is disposed about a substantial portion of the length of rod 14 for electrically insulating rod 14 from the environment.

In one embodiment of the method of the present invention, penetrator 12 is directed into organism 22 to place first electrode 18 adjacent to contact with tissue 24 which is to be electroporated. Penetrator 12 has a suitable diameter for insertion into an organism without harming the organism. In one embodiment the diameter of penetrator 12 is in the range of between about 0.15 and about 0.3 cm. The length of penetrator 12 is sufficient to reach tissue 24 which is remotely disposed within organism 22 from skin 26 of organism 22.

Second electrode 28 of apparatus 10 is disposed at skin 26 of the organism, whereby a voltage applied between first electrode 18 within tissue 24 and second electrode 28 at skin 26 will cause electroporation of tissue 24 proximate to first electrode 18. Preferably, second electrode 28 has a surface area in contact with skin 26 which is at least one hundred fold the surface area of first electrode 18. Causing second electrode 28 to be significantly larger than first electrode 18 results in the desirable feature of allowing a substantial portion of the electroporation to occur at first electrode 18. In an alternate embodiment, second electrode 28 can be disposed at the end of a penetrator, not shown, which is directed into the organism, rather than disposed at the surface of skin 26.

Rod 14 is connected to electrical pulse generator 30 by wire 32. Second electrode 28 is connected to electrical pulse generator 30 by wire 34. Electrical pulse generator 30 is suitable for generating pulses of voltage between first electrode 18 and second electrode 28 which are sufficient to cause electroporation of tissue 24 proximate to first electrode 18. An example of a suitable electrical pulse generator is an electrical pulse generator which is able to deliver an exponential pulse having a 0.3 millisecond time constant and a peak value of 300 volts. Alternatively, an alternating voltage generator can be employed, whereby an alternating voltage is applied between first electrode 18 and second electrode 28 which is sufficient to cause electroporation of tissue 24. It is to be understood that, alternatively, electrical current generators can be employed to generate a suitable voltage across tissue 24.

A suitable chemical agent for treatment of tissue 24 is directed into blood vessel 36 of organism 22 which supplies blood to tissue 24. Examples of suitable chemicals include: chemotherapeutic agents; DNA; antimicrobial agents, such as antiviral agents, antifungal agents, antiparasitic agents and antibacterial agents; drugs; toxins; etc. Alternatively, chemical agents, such as substantially pure water, physiological saline or dilute physiological saline can be employed for killing at least a portion of the cells of the electroporated tissue.

The chemical agent is injected into blood vessel 36 by introducing hypodermic syringe 38 into blood vessel and injecting chemical agent 40 through hypodermic needle 42 of hypodermic syringe 38 into bloodstream 44. In a preferred embodiment, injection of chemical agent 40 into bloodstream 44 and generation of electrical pulses are coordinated so that tissue 24 is electroporated at about the same time that chemical agent 40 reaches tissue 24 from the point of injection.

For example, chemical agent 40 can be injected into blood vessel 36 at a point distant from tissue 24, as shown in FIG. 1. In this embodiment, activation of electrical pulse generator 30 to cause electroporation of tissue 24 at first electrode 18 can be delayed for a period of time following injection of chemical agent 40 sufficient to cause electroporation of tissue 24 at about the same time that chemical agent 40 reaches tissue 24. A suitable method for calculating the period of time between injection and delivery of chemical agent 40 to tissue 24 includes relating the distance between the point of injection and tissue 24 to the rate of blood flow through blood vessel 36.

The voltage applied between first electrode 18 of penetrator 12 and second electrode 28 is sufficient to cause electroporation of tissue 24 and thereby allow migration of chemical agent 40 at tissue 24 across cell membranes of tissue 24. Tissue 24 is thereby treated by chemical agent 40. Preferably, the amount of voltage applied between first electrode 18 and second electrode 28 is in the range of between about one hundred and about one thousand volts. In a particularly preferred embodiment, the pulses generated by electrical pulse generator are exponential pulses having a time constant in the range of between about 0.1 and about one millisecond and an amplitude in the range of between about one hundred and about one thousand volts. Typically, the number of pulses sufficient to cause electroporation is in the range of between about one and about ten, wherein the interval between pulses is in the range of between about 0.01 and about one second.

"Electroporation," as that is used herein, means increased permeability, of a cell membrane and/or at least a portion of cells of a targeted tissue, to a chemical agent, wherein the increased permeability is caused by application of voltage across the cell or at least a portion of the tissue. The chemical agent can thereby migrate into the electroporated tissue and/or across the cell membrane and into the cell. Electroporation can include, for example, killing at least a portion of the cells of targeted tissue to thereby cause the permeability of the tissue to significantly increase.

Although the mechanism of the invention is not completely understood, it is believed that migration of a chemical agent into tissue and across cell membranes into cells can occur by passive and active transport.

Passive transport includes diffusion into the tissue and/or through cell membranes. Active transport includes direction of a chemical agent into the tissue and/or through cell membranes by a driving force, such as convective flow or electrical drift. During convective flow, for example, the chemical agent is directed into tissue and/or through cell membranes in response to differences in pressures, such as hydrostatic pressure, electro-osmotic pressure and osmotic pressure. Electrical drift includes movement of chemical agents, such as ions and/or charged molecules, into electroporated tissue and cells in response to a local electric field which is at the targeted electroporated area. It is to be understood, that the chemical agent can, in suitable applications, be electrically charged to allow migration during electroporation by electrical drift.

In one embodiment, the electrical pulse, or pulses, generated by electrical pulse generator 30 is sufficient to also cause electroporation of blood vessel 36. Chemical agent 40 can thereby migrate across the tissue of blood vessel 36 into tissue 24. Alternatively, chemical agent 40 can be injected into blood vessel 36 at a point close to tissue 24 or at tissue 24 before or during electroporation of at least a portion of tissue 24. Typically, a voltage is applied across tissue 24 by electrical pulse generator within about ten seconds of injection of chemical agent 40 into tissue 24. Electroporation of tissue 24 caused by the voltage applied between first electrode 18 and second electrode 28 allows chemical agent 40 to migrate across tissue 24 and then across the cell membranes of at least a portion of the cells which comprise tissue 24, thereby entering the cells and treating tissue 24.

It is to be understood that tissue 24 can include cells which are native to organism 22, such as healthy or diseased organ tissue, or can be foreign organisms. Examples of foreign organisms which can be treated by the method apparatus of the invention include infectious microorganisms, fungi, parasites, etc. Foreign cells and microorganisms can also be treated which are not disposed within another organism, such as foreign cells or colonies disposed at the surface of another organism, or disposed on an inanimate support.

It is also to be understood that, for suitable applications, tissue 24 can be treated by electroporating tissue 24 with apparatus 10 without introducing a chemical agent to organism 22 for migration across cell membranes of tissue 24. For example, the chemical agent which migrates across the cell membranes of cells in tissue 24 can be a suitable naturally-occurring chemical agent which is produced by the organism, such as a hormone.

The chemical agent to be used to treat tissue 24 can also be introduced to organism 22 by other suitable methods. For example, the chemical agent can be injected directly into tissue 24 rather than into a blood vessel which delivers the chemical agent to tissue 24. Also, the chemical agent can be delivered from a reservoir of the chemical agent which is disposed within organism 22. In one embodiment, the reservoir is formed by an intramuscular injection or subcutaneous injection of the chemical agent into organism 22. In another embodiment, the chemical agent can be released into organism 22 from a capsule which is disposed within organism 22. Suitable capsules are disclosed for example, in U.S. Pat. No. 4,863,735, issued to Kohn et al., the teachings of which are incorporated herein by reference. The chemical agent can also be introduced to the organism by forming a composition which includes the chemical agent and which is suitable for topical application and absorption of the composition through the skin of the organism into the bloodstream.

Figure 2:
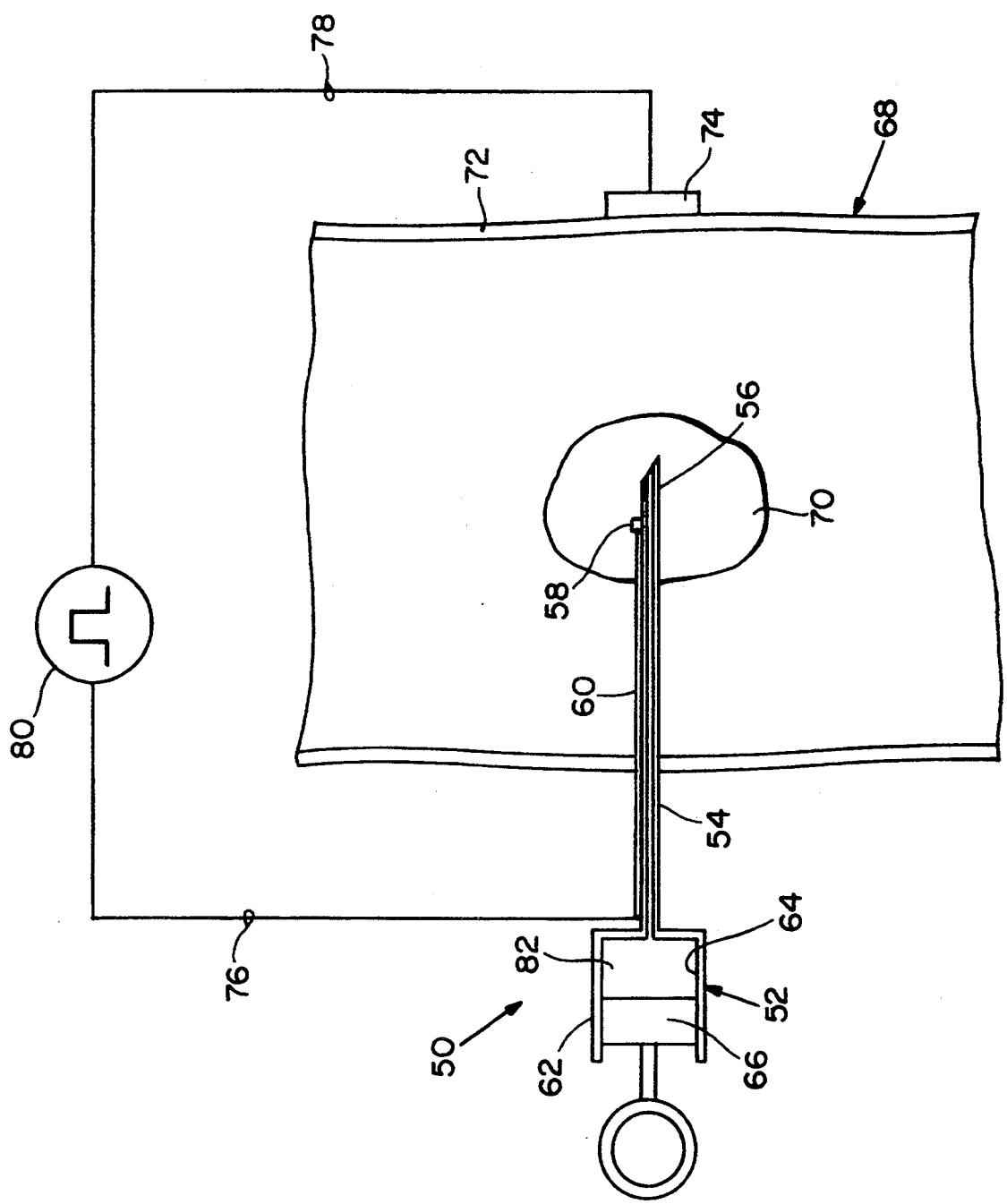
FIG. 2 is a section view of an alternate embodiment of the invention which includes a catheter and an electrode disposed at the catheter.

In another embodiment, shown in FIG. 2, electroporation apparatus 50 includes penetrator 52. Penetrator 52 includes catheter 54 which has a penetrating end 56 suitable for insertion of catheter 54 into an organism without significantly harming the organism.

Catheter electrode 58 is disposed at penetrating end 56 of catheter 54. Insulated wire 60 is disposed along catheter 54 for applying an electrical pulse along catheter 54 to catheter electrode 58. Alternatively, catheter 54 can be formed of an electrically conductive material whereby a voltage is applied between catheter 54 and catheter electrode 58. In this embodiment, an electrically insulating sheath, not shown, is disposed about catheter 54 to shield surrounding tissue from catheter 54.

Housing 62 is disposed at catheter 54 and defines housing chamber 64. Plunger 66 is disposed within housing chamber 64 and is moveable within housing 64 for delivery of a chemical agent from housing chamber 64 through catheter 54.

Catheter 54 is directed into organism 68, whereby catheter electrode 58 and penetrating end of catheter 54 are disposed proximate to tissue 70. Preferably, penetrating end 56 and catheter electrode 58 are in contact with tissue 70. Surface electrode 74 is placed at a location on skin 72 of organism 68, whereby a suitable voltage pulse, or pulses, applied between catheter electrode 58 and surface electrode 74, will cause electroporation of tissue 70. Wires 76,78 extend from insulated wire 60 and second electrode 74, respectively, to electrical pulse generator 80 for providing an electrical connection between electrical impulse generator 80 and electrodes 58,74.

A suitable chemical agent 82, disposed within housing chamber 64, is displaced from housing chamber 64 by depressing plunger 66 against chemical agent 82. Chemical agent 82 is thereby directed from housing chamber 64 through catheter 54 to tissue 70.

Electrical pulse generator 80 is activated to cause at least one voltage pulse between catheter electrode 58 and surface electrode 74. The voltage applied between catheter electrode 58 and surface electrode 74 is sufficient to cause electroporation of tissue 70. Chemical agent 82, which has been delivered by penetrator 52 to tissue 70, migrates across cell membranes of cells comprising tissue 70 and into the cells, thereby treating tissue 70. It is to be understood, however, that chemical agent 82 can be delivered by penetrator 52 to tissue 70 before, during, and/or after electroporation of tissue 70 has been initiated.

It is also to be understood that catheter electrode 58 can be configured for different applications. For example, catheter electrode 58 can be configured as a spherical section to cause electrical fields generated by the applied voltage at catheter electrode 58 to be symmetrically distributed about catheter electrode 58. Electroporation of tissue 70 surrounding catheter electrode 58, therefore, can be more symmetrically distributed. Alternatively, catheter electrode 58 can be configured to cause the electric field at catheter electrode 58 to be substantially distributed in only a single direction, to thereby cause a disproportionate amount of electroporation to occur in one direction from catheter electrode 58. Tissue 70 about catheter electrode 58 can thereby be selectively electroporated and treated by the method of the invention.

In still another embodiment of the apparatus of the invention, shown in FIG. 3, electroporation apparatus 90 includes endoscope 92. Endoscope 92 includes end portion 94 at which endoscope electrode 96 is disposed. Insulated wire 98 extends from endoscope electrode 96 along endoscope 92.

Endoscope 92 is inserted into patient 100 through breathing passage 102 into lung 104, to a position within lung 104 proximate to tissue 106, which is to be treated by the method of the invention. Fluid 108 is disposed within lung 104 to a level sufficient to immerse tissue 106 and endoscope electrode 96. Fluid 108 is sufficiently electrically conductive to allow a voltage applied across fluid 108 to electroporate tissue 106. Examples of suitable fluids include water, physiologic saline, artificial blood substitutes, etc. It is to be understood that endoscope electrode 96 can be in contact with tissue 106. It is also to be understood that fluid 108 need not be employed in applications where an electrically conductive contact can be formed between endoscope electrode 96 and tissue 106. For example, in some applications, an electrically conductive material, such as an electrically conductive ointment or paste, can be disposed on endoscope electrode 96 for forming an electrically conductive contact between endoscope electrode 96 and tissue 106.

Second electrode 110 is disposed on the surface of skin 112 of patient 100, at a position which allows a voltage applied between endoscope electrode 96 and second electrode 110 to cause electroporation of tissue 106. Wires 114,116 provide electrical connections between insulated wire 98 and second electrode 110, respectively, and electrical pulse generator 118. A suitable chemical agent is introduced to tissue 106 for treatment of tissue 106 by the method of the invention. An example of a typical method for introducing the chemical agent is by employing syringe 120 to inject the chemical agent directly into tissue 106. Electrical pulse generator 118 is activated to apply a voltage across tissue 106 and thereby cause electroporation of tissue 106. The chemical agent in tissue 106 thereby migrates across cell membranes of cells within tissue 106 to treat tissue 106.

It is to be understood that endoscope 92 can be employed to treat tissue which is accessible through other body passages and disposed within other body cavities. Examples of suitable body passages include: nasal passages; the alimentary canal; blood vessels; ducts, such as tear ducts; etc.

In still another embodiment of the present invention, shown in FIG. 4, apparatus 130 includes penetrator 132. First electrode 138 is disposed at end 134 of penetrator 132. Second electrode 140 is disposed at a spaced interval from first electrode 138 along penetrator 132. Insulated wires 142,144 connect first electrode 138 and second electrode 140 to electrical pulse generator 146, respectively. Activation of electrical pulse generator 146 either before, during or after injection of a suitable chemical agent into targeted tissue, causes a voltage to be applied between first electrode 138 and second electrode 140. A chemical agent is injected either into the tissue to be electroporated or at a remote location for transport through the blood stream of the organism to the tissue. At least a portion of tissue at or near first electrode 138 and second electrode 140 is thereby electroporated, whereby the chemical agent injected by penetrator 132 migrates into at least a portion of the tissue and/or across the cell membrane of at least one of the cells of the tissue and into the cell, thereby treating the tissue or cell.

In another alternative embodiment, shown in FIG. 5, apparatus 147 includes penetrator 148. Penetrator 148 defines orifice 150, which is disposed between first electrode 152 and second electrode 154. It is to be understood, however, that orifice 150 can be disposed along penetrator 148 on either side of the electrodes, rather than between them. Penetrator 148 is formed of a suitable electrically non-conductive material. First electrode 152 and second electrode 154 are disposed at a spaced interval at penetrator 148 and are connected to electrical pulse generator 156 by insulated wires 158,160, respectively. Activation of electrical pulse generator 156 causes electroporation of at least a portion of tissue at or near first electrode 152 and second electrode 154, whereby a suitable chemical agent, which is injected through penetrator 148 and orifice 150, is allowed to migrate into the tissue and/or cells.

In all of the above embodiments, it is to be understood that examples of suitable penetrators include a rod, a catheter, an endoscope, etc. Suitable endoscopes include endoscopes which can deliver a chemical agent through a conduit defined by the endoscope.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

I claim:

1. A method for treating at least one cell, in vivo, comprising the steps of:
   a) directing a penetrator into an organism, said penetrator including a first electrode, and an opening through which a chemical agent can be injected into the organism proximate to the cell to be treated;
   b) placing a second electrode where the cell and the opening of the penetrator are between the first and second electrodes;
   c) injecting the chemical agent into the organism through the penetrator in an amount sufficient to treat the cell during electroporation of the cell; and
   d) applying a voltage between the first and second electrodes in an amount sufficient to cause electroporation of at least a portion of the cell, whereby the chemical agent migrates across the cell membrane, thereby treating the cell.

2. A method of claim 1 wherein the chemical agent is injected into tissue which includes the cell.

3. A method of claim 1 wherein the voltage is applied between the first electrode and the second electrode before the chemical agent is injected into the organism.

4. A method of claim 1 wherein the voltage is applied between the first electrode and the second electrode during injection of the chemical agent into the organism.

5. A method of claim 1 wherein the voltage is applied between the first electrode and the second electrode after injection of the chemical agent into the organism.

6. A method of claim 1 wherein the voltage applied between the first electrode and the second electrode includes at least one pulse.

7. A method of claim 1 wherein the chemical agent is injected into an interior conduit of the organism.

8. A method of claim 7 wherein the interior conduit is selected from the group consisting of a blood vessel, a lymph duct, a gastrointestinal tract and a urinary tract.

9. A method of claim 1 wherein the chemical agent is injected into a joint of the organism.

10. A method of claim 1 wherein the chemical agent is injected into an abdominal cavity of the organism.

11. A method of claim 1 wherein the chemical agent is selected from the group consisting of toxins, DNA, drugs, water and physiologic saline.

12. A method of claim 1 wherein the chemical agent includes an antimicrobial agent.

13. A method for treating at least one cell, in vivo, comprising the steps of:
   a) directing a catheter into a blood vessel of an organism, said catheter including a first electrode, and an opening through which a chemical can be injected into the organism proximate to the cell to be treated;
   b) placing a second electrode in a position where the cell and the opening of the catheter are between the first and second electrodes;
   c) injecting the chemical into the organism through the catheter in an amount sufficient to treat the cell during electroporation of the cell; and
   d) applying a voltage between the first and second electrodes in an amount sufficient to cause electroporation of at least a portion of the cell, whereby the chemical agent migrates across the cell membrane, thereby treating the cell.

14. A method of claim 13 wherein the blood vessel includes an artificial blood vessel.

15. A method of claim 13 wherein the point of chemical agent injection in the blood vessel allows the chemical agent to pass along the portion of the blood vessel wall which is electroporated after a period of time following injection of the chemical agent, and wherein the voltage applied between the first electrode and the second electrode includes at least one electrical pulse.

16. A method of claim 13 wherein the voltage is applied across the blood vessel wall while the chemical agent passes along the blood vessel wall.

17. A method for treating at least one cell, in vivo, comprising the steps of:
   a) directing an endoscope into a blood vessel of an organism, said endoscope including a first electrode, and an opening through which a chemical can be injected into the organism proximate to the cell to be treated;
   b) placing a second electrode in a position where the cell and the opening of the endoscope are between the first and second electrodes;
   c) injecting the chemical into the organism through the endoscope in an amount sufficient to treat the cell during electroporation of the cell; and
   d) applying a voltage between the first and second electrodes in an amount sufficient to cause electroporation of at least a portion of the cell, whereby the chemical agent migrates across the cell membrane, thereby treating the cell.

18. An apparatus for treating at least one cell, comprising:
   a) a penetrator having a penetrating end, for penetration of an organism, and an opening through which a chemical agent can be injected into the organism proximate to the cell to be treated;
   b) a first electrode at the penetrating end;
   c) a second electrode located on the penetrator at a spaced interval from the first electrode wherein the opening is between the first and second electrodes; and
   d) means connected to the first and second electrodes for applying a voltage between said electrodes in an amount sufficient to electroporate the cell, whereby said chemical agent in the organism migrates across the cell membrane and into the electroporated cell, thereby treating the cell.

19. An apparatus of claim 18 wherein the penetrator is a catheter.

20. An apparatus of claim 18 wherein the penetrator is an endoscope.

21. An apparatus of claim 18 wherein the surface area of the second electrode is larger than the surface area of the first electrode, whereby a substantial portion of the electroporation will occur at cells of the organism proximate to the first electrode.

22. An apparatus for treating at least one cell of an organism with a chemical agent, comprising:
   a) a penetrator for penetration of a organism having a penetrating end;
   b) a first electrode disposed at the penetrating end of the penetrator whereby the first electrode is disposed adjacent to the cell when the penetrator penetrates the organism;
   c) a second electrode for applying a voltage between the first and second electrodes to cause electroporation of the cell;
   d) a porous member for introducing the chemical agent into the organism, whereby disposing the porous member in the organism causes the chemical agent to migrate from the porous member to the cell for treatment of the cell during electroporation; and
   e) means connected to the first and second electrodes for applying a voltage between said electrodes in an amount sufficient to electroporate the cell, whereby the chemical agent in the organism migrates across the cell membrane and into the electroporated cell, thereby treating the cell.

23. In a method for treating at least one cell with a chemical agent by electroporation which includes directing a chemical agent into the organism in an amount sufficient to treat the cell during electroporation of the cell:
   The improvement comprising directing a penetrator into an organism, said penetrator including a first electrode, and an opening through which the chemical agent can be injected into the organism proximate to the cell, placing a second electrode in a position where said second electrode causes the cell and the opening of the penetrator are between the first and second electrodes, injecting the chemical agent into the organism through the penetrator in an amount sufficient to treat the cell during electroporation of the cell, and applying a voltage between the first and second electrodes in an amount sufficient to cause electroporation of at least a portion of the cell, whereby the chemical agent migrates across the cell membrane, thereby treating the cell.

* * * * *